United States Patent [19]

Abramowitz

[11] Patent Number: 5,199,946
[45] Date of Patent: Apr. 6, 1993

[54] DEVICE AND METHOD FOR ADMINISTERING INTERPLEURAL ANESTHESIA

[76] Inventor: Joseph Abramowitz, 18 Covert St., Port Washington, N.Y. 11050

[21] Appl. No.: 719,150

[22] Filed: Jun. 21, 1991

[51] Int. Cl.$^5$ .............................................. A61M 31/00
[52] U.S. Cl. ....................................... 604/51; 604/239; 604/272; 128/898; 606/190
[58] Field of Search ........................ 604/48, 49, 51, 52, 604/53, 239, 272, 273, 275, 187, 218; 128/898; 606/190, 166, 159

[56] References Cited

U.S. PATENT DOCUMENTS

| | | | |
|---|---|---|---|
| 2,922,420 | 1/1960 | Cheng | 604/272 |
| 2,952,256 | 9/1960 | Meader et al. | 604/272 |
| 3,506,007 | 4/1970 | Henkin | 604/51 |
| 3,630,198 | 12/1971 | Henkin | 604/170 |
| 3,854,477 | 12/1974 | Smith | 604/51 |
| 3,960,153 | 6/1976 | Carey et al. | 604/164 |
| 4,186,750 | 2/1980 | Patel | 604/272 X |
| 4,721,506 | 1/1988 | Teves | 604/51 |
| 4,813,929 | 3/1989 | Semrad | 604/51 |
| 4,844,087 | 7/1989 | Garg | 128/753 |
| 4,908,015 | 3/1990 | Anis | 604/22 |
| 4,950,233 | 8/1990 | Abramowitz | 604/51 |
| 5,019,039 | 5/1991 | Anderson | 604/51 |

FOREIGN PATENT DOCUMENTS

| | | | |
|---|---|---|---|
| 0232678 | 8/1987 | European Pat. Off. | 606/159 |
| 3019115 | 12/1981 | Fed. Rep. of Germany | 606/159 |
| 3421390 | 12/1985 | Fed. Rep. of Germany | 606/159 |

*Primary Examiner*—C. Fred Rosenbaum
*Assistant Examiner*—Mark O. Polutta

[57] ABSTRACT

Using a safe blunt-nosed hyperdermic needle an anesthetizing fluid is deposited in a patient's pleural space by clearing the passage for the advance of the needle using the pressure of the anesthetizing fluid and the swelling of tissue which it causes.

2 Claims, 1 Drawing Sheet

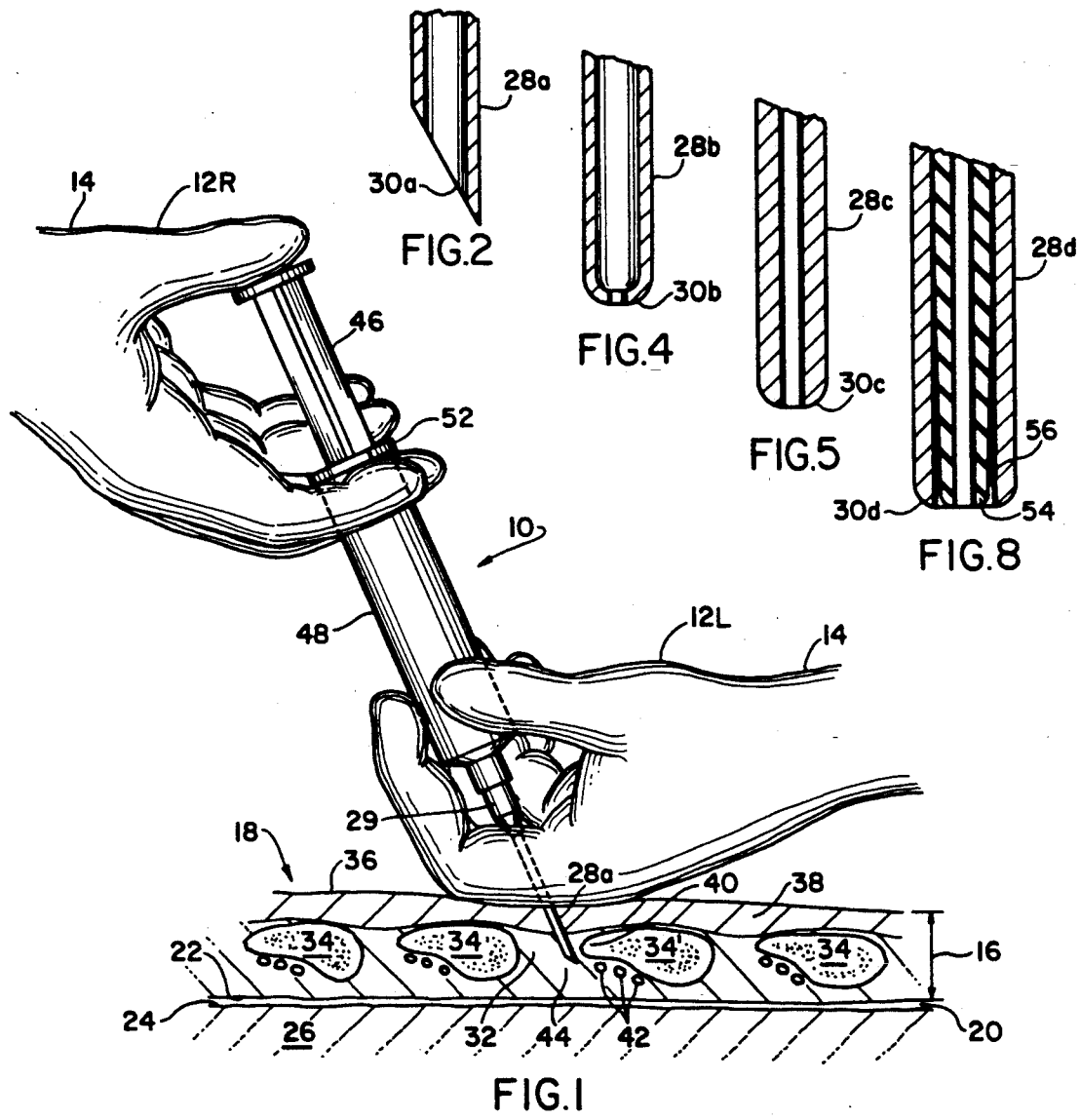
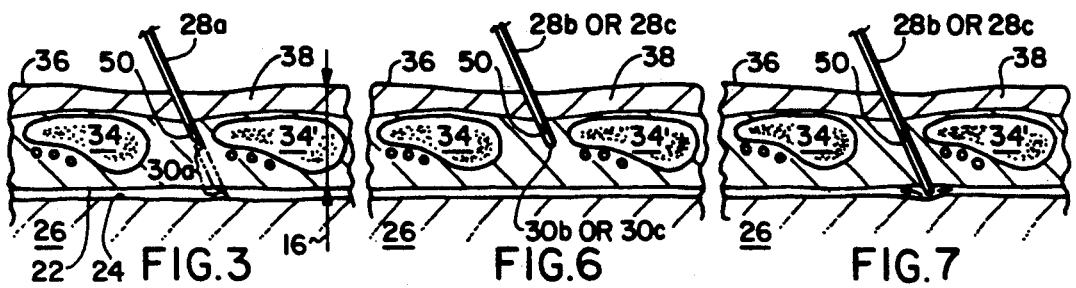

5,199,946

DEVICE AND METHOD FOR ADMINISTERING INTERPLEURAL ANESTHESIA

The present invention relates an improved method for administering an anesthetizing fluid in a patient's pleural space, without risk of puncturing the visceral pleura which bounds this space on the far side, and which long was a danger in prior art methods.

EXAMPLES OF THE PRIOR ART

In U.S. Pat. No. 3,630,198 issued on Dec. 28, 1971 to Henkin, there is disclosed the danger of using a pointed needle as a result of inadvertent "puncturing of delicate tissue and organs disposed in the path of the needle, ... beyond the intended area of penetration" (col. 1, lines 25-28). It is suggested that a safer needle be substituted, but no method or mode of use thereof is correspondingly suggested to make this substitution workable.

In U.S. Pat. No. 4,529,399 issued Jul. 16, 1985 to Groshong, et al., a method of inserting a sharp tipped catheter is described while noting that "fluid is simultaneously infused into the body vessel to dilate it and thereby ease the advancement of the catheter with minimal damage to the vessel wall" (See "Abstract"). The noted use of fluid notwithstanding, the method of this patent continues, or at least does not dispense with, the use of the potentially dangerous sharp tip of the inserted instrument, and thus leaves unsolved the problem identified in the Henkin patent.

SUMMARY OF THE INVENTION

Underlying the present invention is the recognition that a safe blunt nosed instrument can be advanced from an external entry site to an internal medication deposit site and, more particularly, that a sharp nose is not necessary for such advancement, provided that the path of movement is cleared by a selected pressure fluid and a tissue-swelling phenomenon caused by the selected fluid, all as will be better understood from the detailed description of the present invention which now follows.

The description of the invention which follows, together with the accompanying drawings should not be construed as limiting the invention to the example shown and described, because those skilled in the art to which this invention appertains will be able to devise other forms thereof within the ambit of the appended claims.

BRIEF DESCRIPTION OF THE DRAWINGS

FIG. 1 is an elevational view, illustrating a patient's anatomy in section, and showing the prior art method of administering interpleural anesthesia, for contrast with the within improved method of the present invention;

FIG. 2 is a detailed sectional view of the distal end of a sharp-nosed needle of a hyperdermic syringe used in the prior art anesthetizing method;

FIG. 3 is a sectional view similar to FIG. 1, showing the sharp-nosed hyperdermic needle of FIG. 2 at succeeding positions of movement;

FIG. 4 and 5 are detailed sectional views of the distal end of two embodiments of blunt-nosed hyperdermic needles used in the within inventive method;

FIGS. 6 and 7 are cross sectional views similar to FIG. 3 showing succeeding positions of movement of the hyperdermic needles of FIGS. 4 and 5; and FIG. 8 is a detailed sectioned view showing the distal end of a blunt-nosed hyperdermic needle of the type shown in FIGS. 4 and 5, but modified in diameter for use as a cannula preparatory to the introduction of a catheter into the patient.

DESCRIPTION OF THE PREFERRED EMBODIMENTS

Shown in FIG. 1 is a typical hyperdermic syringe 10 in its position being manipulated by the hands 12 of a highly qualified medical person or doctor 14 during penetration of the chest wall 16 of a patient 18. The illustrated procedure will be understood to provide access to the pleural space 20 of the patient preparatory to the infusion of an anesthetizing fluid therein incident to extracting accumulated fluids from the pleural space 20.

As further understood, the so-called pleural space 20 is the separation between the inner face 22 or parietal pleura of the chest wall 16 and the outer face 24 or visceral pleura of the lung 26. These adjacent surfaces 22 and 24 of the pleural space are smooth and moistened by a serous fluid.

Illustrating the prior practice in FIG. 1, it is to be noted that syringe 10 is fitted with a sharp-nosed needle 28a having a conventional coupling means 29 and wherein the sharp-nose of the needle is formed by a conventional angled tip 30a, as shown in FIG. 2. The doctor-user 14 initiates the procedure by first locating an appropriately selected entry site above the intercostal space 32 and between a pair of ribs 34. Tip 30a of needle 28a is then used to pierce skin 36 adjacent the lower edge 40 of rib 34' and penetrate subcutaneous tissue 38. Tip 30a is guided inwardly along a penetrating path of movement around the lower edge 40 of rib 34,; during which extreme care is required to be taken to avoid intercepting or penetrating neurovascular bundle 42 within the intercostal groove beneath rib 34'. Tip 30a is then advanced in movement, being guided by the doctor's hand 14 at the distal end of the syringe 10, through the intercostal muscle layers 44 to a depth appropriate for the anesthesia deposit site at which the needle penetrates the parietal pleura 22. As tip 30a enters the pleural space 20 it is incumbent upon the doctor 14 to sense a subtle loss of resistance to advancement of the needle and to stop such advancement when this is sensed. Otherwise further advancement of tip 30a will result in puncture of tissue, i.e., the visceral pleura 24, as shown in phantom perspective in FIG. 3, which puncture may cause an air leak from lung 26 and possibly result in a potentially fatal lung collapse.

Completing the prior art method, tip 30a is now carefully held in position in the pleural space 20 while plunger 46 is urged through a power stroke resulting in the discharge or deposit of anesthetizing fluid exiting from syringe barrel 48 at the deposit site 24. Upon completion of the desired measured amount of anesthetizing fluid, syringe 10 along with, of course, its needle 28a, is removed from the patient 18.

In sharp contrast to the foregoing described method, in the practice of the within inventive method a sharp-nosed needle 28a is used on a syringe 10 only initially to penetrate at a selected entry site the skin 36 and to a shallow depth adjacent thereto of the subcutaneous tissue 38 of the patient 18, such initial shallow penetration being shown in solid line in FIG. 3. After piercing skin 36, the doctor-user 14 dispenses,using his hand at the proximal end of the syringe by activating plunger 46, a small amount of anesthetic fluid, e.g. bupivacaine, as the tip 30a is advanced about half way through chest wall 16. During the needle 28a penetration as just described and as a consequence of the infusion or deposit of anesthetic fluid, there is a swelling of muscle tissue which, in effect, is an enlargement of the clearance between muscle fibers in advance of the needle tip 30a, thus creating an entrance passageway 50.

At this point in the interplural anesthetizing method, syringe 10 is withdrawn and needle 28a is replaced with a blunt-nosed needle of the type designated and constructed as shown in FIGS. 4 or 5, respectively. Optionally, this needle replacement step can be done immediately after penetration of the hyperdermic needle at the entry site and before significant penetrating movement along the path of movement to the deposit site 24. In this regard, underlying the within inventive method is the recognition that penetration through the patient's tissue 38 as above described does not require a sharp-nosed needle to clear a path, but is readily achieved even with a blunt-nosed needle, because there is being used the pressure of the exiting anesthetizing fluid and also being used to advantage the muscle tissue swelling phenomenon above noted, both of which cooperate to clear out of the way the tissue in advance of the penetrating needle. Thus, it is contemplated that the doctor, after filling the syringe barrel 48 with anesthetizing fluid, may elect to attach a blunt-nosed needle of the type denoted as 28b or 28c in forwarding extending position from the syringe end, and while guiding with his one hand at the distal syringe end and activating the plunger 46 with his other hand, effectively move the blunt-nosed needle 28b, 28c from the entry site 36 to the deposit site 22, 24, using the blunt-nosed needle because of its greater safety, relying on the pressure of the exiting fluid and tissue swelling to clear the way for this non-cutting needle nose.

Continuing with the description of the equipment or components used in practicing the inventive method, it is to be noted that needles 28b and 28c have respective tips 30b and 30c both of which can be characterized as "blunt" as opposed to the "sharp" shape of needle tip 28a. In use, the blunt tip 30b or 30c is inserted within entrance passageway 50 (FIG. 6). The dispensing of a small amount of anesthesia is renewal as the needle tip 30b and 30c is advanced further through chest wall 16. Advancement is continued as long as resistance is felt, but is stopped when there is a perceived "loss" of resistance which indicates the tip of the needle has penetrated the chest wall 16 and is in the pleural space 20 (FIG. 7).

It is to be noted that the blunt tip 30b or 30c may inadvertently advance beyond the parietal pleura 22 to the visceral pleura 24 without the immediate danger of puncture thereof. Assuming that the administration of anesthesia to the pleural space 20 is the reason for the procedure, it would follow that the measured amount thereof is to be infused or deposited at the site 22, 24. If the reason for the procedure is other than the delivery of anesthesia to the pleural space 20, however, then needle 28b or 28c is advantageously disconnected and reconnected to an appropriate intravenous system or hyperdermic syringe with other medication while remaining in passage 50.

In carrying out the within inventive method or procedure, a preferred handling of syringe 10 has been developed where the thumb, forefinger and middle finger of the non-dominant hand 12L is used to firmly grasp the barrel 48 of syringe 10 while the back of hand 12L rests against the patient 18 (FIG.1). The shank of the needle 28a, b or c is within the crotch of the fore and middle fingers. The syringe plunger 46 is operated by the dominant hand 12R in the usual manner, wherein the thumb is used to apply force in opposition to the fore and middle fingers which bear against the barrel flange 52.

Should it be necessary to introduce a catheter 54 within the pleural space 20, needle 28b or 28c is withdrawn from patient 18 and a substitute needle 28d introduced into the anesthetized entrance passage 50. Needle 28d has a blunt tip 30d and a bore 56 of large enough diameter to allow passage therethrough of a catheter 54. Once needle 28d is in place in patient 18, it is used as a cannula to introduce catheter 54 within pleural space 20 for the infusion or effusion of fluids. After the placement of catheter 54, needle 28d can be removed and catheter 54 can be taped or otherwise held in place against the patient's skin 36.

Although the above described technique or method and devices for its practice were specifically developed for interpleural anesthesia in connection with contemplated surgery, they may readily be extended to include the treatment and diagnosis of many pleural disorders.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method for a doctor to administer interpleural anesthesia to a patient using a hypodermic syringe of a type having opposite proximal and distal ends and an operational mode of forcing fluid under pressure from a needle forwardly extending therefrom in response to a power stroke of a plunger of said syringe, said method comprising the steps of selecting a site of entry for said needle in the patient's skin that is in a clearance location from a selected site of deposit of interpleural anesthesia, attaching in said forwardly extending position from said hypodermic syringe a blunt-nosed needle having fluid communication with said syringe, filling said springe with an anesthetizing fluid, inserting said blunt-nosed needle in said entry site to a preliminary depth in close proximity to said deposit site, holding said distal and proximal ends of said hypodermic syringe, guiding at the distal end of said hypodermic syringe the forwardly extending needle thereof along a path of movement from said entry site towards said deposit site, and forcing under pressure said anesthetizing fluid by activating at said proximal end said syringe plunger to cause exiting flow of said anesthetizing fluid from said blunt-nosed needle during the advancement of said blunt-nosed needle along said path of movement, whereby said exiting pressure of said anesthetizing fluid clears a path for said needle advancement although said needle is blunt-nosed to thereby obviate any inadvertent tissue punctures that otherwise might result at said deposit site using a sharp-nosed needle.

2. A method for a doctor to administer interpleural anesthesia to a patient using a hypodermic syringe of a type having opposite proximal and distal ends and an operational mode of forcing fluid under pressure from a needle forwardly extending therefrom in response to a power stroke of a plunger of said syringe, said method contemplating a selected site of entry for said needle in the patient's skin that is in a clearance location from a selected site of deposit of interpleural anesthesia, said method comprising the steps of attaching in said forwardly extending position from said hypodermic syringe a sharp-nosed needle having fluid communication with said syringe, filling said syringe with an anesthetizing fluid, inserting said sharp-nosed needle in said entry site to a preliminary depth in close proximity to said deposit site, withdrawing said hypodermic syringe and replacing said sharp-nosed needle thereof with a blunt-nosed needle and again inserting same in said entry site of said patient, holding at the respective distal and proximal ends said hypodermic syringe, guiding at the distal end of said hypodermic syringe the path of movement of said blunt-nosed needle from said entry site towards said deposit site, and forcing under pressure said anesthetizing fluid by activating at said proximal end said syringe plunger to cause exiting flow of said anesthetizing fluid from said blunt-nosed needle during the advancement of said blunt-nosed needle along said path of movement, whereby said exiting pressure of said anesthetizing fluid clears a path for said needle advancement although said needle is blunt-nosed to thereby obviate any inadvertent tissue punctures that otherwise might result at said deposit site using a sharp-nosed needle.

* * * * *